ized States Patent (12)
Zhu et al.

(10) Patent No.: US 9,232,787 B2
(45) Date of Patent: Jan. 12, 2016

(54) VISCOELASTIC SURFACTANT AS DRIFT CONTROL AGENT IN PESTICIDE FORMULATIONS

(75) Inventors: Shawn Zhu, Stormville, NY (US); Michael Walters, Rhinebeck, NY (US)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 83 days.

(21) Appl. No.: 13/992,808

(22) PCT Filed: Dec. 7, 2011

(86) PCT No.: PCT/EP2011/072000
§ 371 (c)(1),
(2), (4) Date: Jun. 10, 2013

(87) PCT Pub. No.: WO2012/076567
PCT Pub. Date: Jun. 14, 2012

(65) Prior Publication Data
US 2013/0260998 A1 Oct. 3, 2013

Related U.S. Application Data

(60) Provisional application No. 61/421,858, filed on Dec. 10, 2010.

(30) Foreign Application Priority Data

Apr. 6, 2011 (EP) .................................. 11161360

(51) Int. Cl.
*A01N 25/30* (2006.01)
(52) U.S. Cl.
CPC ...................... *A01N 25/30* (2013.01)
(58) Field of Classification Search
CPC ....... A01N 25/30; A01N 37/40; A01N 43/40; A01N 57/20
USPC .................. 504/206, 234; 514/788
See application file for complete search history.

(56) References Cited

U.S. PATENT DOCUMENTS

| 3,373,107 A * | 3/1968 | Rice et al. .............. 507/245 |
| 4,770,814 A | 9/1988 | Rose et al. |
| 4,844,734 A | 7/1989 | Iwasaki et al. |
| 5,550,224 A | 8/1996 | Hazen |
| 2010/0009937 A1 | 1/2010 | Elsik et al. |
| 2011/0166235 A1 | 7/2011 | Sun |
| 2012/0065068 A1 | 3/2012 | Downer et al. |
| 2013/0260998 A1 | 10/2013 | Zhu et al. |

FOREIGN PATENT DOCUMENTS

| EP | 0 274 369 A1 | 7/1988 |
| JP | S54-147929 A | 11/1979 |
| JP | S63-022502 A | 1/1988 |
| JP | S63-145205 A | 6/1988 |
| JP | H07-285810 A | 10/1995 |
| JP | H10-505362 A | 5/1998 |
| JP | 2013-537230 A | 9/2013 |
| WO | 97/01281 A1 | 1/1997 |
| WO | 2009/148570 A1 | 12/2009 |
| WO | WO 2010/026127 A1 | 3/2010 |
| WO | 2012/037207 A1 | 3/2012 |
| WO | 2012/076567 A2 | 6/2012 |

OTHER PUBLICATIONS

Office Action issued in Japanese Application No. 2013-542516 dated Jul. 8, 2014 and English translation of same (7 pages).
European Search Report dated Nov. 10, 2011 issued in the corresponding EP Application No. 11161360.0-2103.
International Search Report and the Written Opinion for corresponding International Application No. PCT/EP2011/072000, mailed Sep. 14, 2012.

* cited by examiner

*Primary Examiner* — Sreeni Padmanabhan
*Assistant Examiner* — Yanzhi Zhang
(74) *Attorney, Agent, or Firm* — Norris McLaughlin & Marcus, P.A.

(57) ABSTRACT

Dual function viscoelastic surfactants (VES) which, when used in a pesticide formulation, are capable of producing a spray pattern between the patterns formed by spraying water and an aqueous pesticide solution containing guar gum as a way to reduce the drifting of the small drops to unintended targets while providing enhanced efficacy to the pesticide.

11 Claims, No Drawings

VISCOELASTIC SURFACTANT AS DRIFT CONTROL AGENT IN PESTICIDE FORMULATIONS

This application is a National Stage entry of International Application PCT/EP2011/072000, filed Dec. 7, 2011, which claims the benefit of U.S. Patent Application No. 61/421,858, filed Dec. 10, 2010 and European Patent Application No. 11161360.0, filed Apr. 6, 2011. The contents of the aforementioned applications are incorporated herein by reference in their entireties.

FIELD OF THE INVENTION

The present invention relates to a dual function viscoelastic surfactant (VES) which, when used in a pesticide formulation, is capable of producing a spray pattern between the patterns formed by spraying water and an aqueous pesticide solution containing guar gum as a way to reduce the drifting of the small drops to unintended targets while providing enhanced efficacy to the pesticide.

BACKGROUND OF THE INVENTION

The drift of spray from pesticide applications can expose people, wildlife, and the environment to pesticide residues that can cause health and environmental effects and property damage.

Various alternatives have been proposed in an attempt to reduce the amount of drifting of small droplets during spraying of an aqueous pesticide solution. For example, high molecular weight water soluble polymers such as a guar gum, xanthan gum, polyacrylamide and other ethylenically unsaturated monomers have been used as drift control agents in the agricultural application. It has been generally accepted that polymers which give optimum spray drift control are either non-ionic (e.g., acrylamide homopolymer) or have relatively low anionic content (e.g. 5 to 30 wt. %) and also have relatively high intrinsic viscosity, for instance above 6 dl/g. Guar gum is the most widely used drift control agent in the current world market. Unfortunately, these polymers have various drawbacks. Their solutions tend to show irreversible lose of their utility due to the fact that high molecular weight polymers undergo mechanical degradation of the polymer chain. In addition, typically it takes a long time for the high molecular weight polymers to evenly disperse or dissolve in aqueous liquids which may lead to many large and undissolved particles that could plug the spraying nozzle. In addition, the polymer drift control agents perform only one task to control drift of small droplets during spraying.

Spray pattern plays an important role in small droplets drifting. When water is sprayed, many small liquid droplets form a mist which easily drifts away with wind. When an aqueous spraying solution containing a guar gum is sprayed, the sprayed pattern is modified so that the number of small droplets is much reduced. Reduction of the number of small droplets increases the size of the droplets when the spray volume remains the same. In fact, the size increase in a typical spraying solution containing guar gum as the drift control agent is often too much so that there are a lot of coarse droplets which tend to bounce off the plant leave and be wasted. Over the years, researchers have found out that the optimum spray pattern has a droplet size distribution between 100-400 m.

There is a need to develop a surfactant based drift control agent capable of reducing the drifting of the small spraying drops as well as enhancing the efficacy of the pesticide without excessive large number of coarse droplets during spraying. Various surfactants are well known to enhance pesticide efficacy by modifying the surface tension of water leading to increased wetting, penetration, and absorption on the surfaces of targeted species.

U.S. Pat. No. 4,770,814 disclosed an anti-misting agent using a VES pair consisting of alkyl trimethyl quaternary surfactant and a organic acid as its counterion and a organic salt with the same ion. Example 1 (sample #2) in the document disclosed a herbicide composition containing 99.4% deionized water, 0.23% cetyltrimethylammonium salicylate, 0.27 sodium salicylate, and 0.1% 2,4-D acid herbicide. This composition was shown to reduce the number of small-sized droplets relative to the sample containing only water.

SUMMARY OF THE INVENTION

The present invention relates to a dual function viscoelastic surfactant (VES) which, when used in a pesticide formulation, is capable of producing a spray pattern between the patterns formed by spraying water and an aqueous pesticide solution containing guar gum. The VES are nitrogen containing surfactants known as alkoxylated alkyl quaternary surfactant, alkyl amine oxide including its alkoxylated derivatives, alkyl betaine including its alkoxylated derivatives, alkyl amidoamine (especially dimethylpropylamidoamine) including its alkoxylated derivatives, alkyl amidoamine (especially dimethylpropylamidoamine) quaternary surfactant including its alkoxylated derivatives, alkyl amidoamine (especially dimethylpropylamidoamine) oxide surfactant including its alkoxylated derivatives, and alkyl amidoamine (especially dimethylpropylamidoamine) betaine surfactant including its alkoxylated derivatives.

DETAILED DESCRIPTION OF THE INVENTION

The present invention generally relates to a composition and method for imparting shear stable anti-drifting properties to aqueous pesticidal formulations through the use of one or more VES. More specifically, the present invention relates to compositions comprising at least one nitrogen based VES in a pesticide formulation where the VES is capable of producing a spray pattern between the patterns formed by spraying water and spraying an aqueous pesticide solution containing guar gum with reduced number of small-sized droplets and coarse droplets size while providing enhanced efficacy to the pesticide.

The following classes of nitrogen containing VES are useful as drift control agents in pesticide formulations according to the invention.

$$R-(AO)_m N^+ \begin{matrix} (AO)_n H \\ \\ (AO)_b H \end{matrix} -Z \quad X^- \quad (A)$$

where R is C12 to C22 linear or branched, saturated or unsaturated hydrocarbon group; AO is C1-C3 alkylene oxide; m=0-3; n=1-3; b=1-3; Z is nothing (or a pair of electron), $C_1$-$C_4$ alkyl, hydroxyl alkyl, oxygen, or $CH_2COO$; $X^-$ is an suitable anion (N bears a positive charge in this case) or nothing when Z is nothing (or a pair of electron), a oxygen or $CH_2COO$;

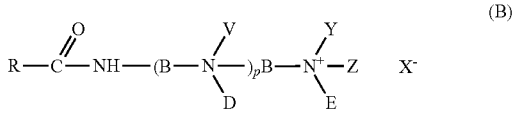

(B)

where R is C12-C22 linear or branched, saturated or nonsaturated hydrocarbon group; B=C2-C6 alkylene; p=0-5; V, D, Y, Z, and E independently is nothing (or a pair of electrons), H (hydrogen), C1-C4 alkyl, or a polyalkoxide group with 1 to 3 alkoxide units with the provisos that (1) V and D can not be both nothing at the same time and (2) the selection of Y, Z, and E only allows the end nitrogen atom to be tertiary or quaternary; $X^-$ is a suitable anion(s).

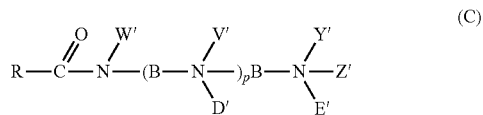

(C)

where R is C12-C22 linear or branched, saturated or nonsaturated hydrocarbon group; B=C2-C6 alkylene; p=0-5; W is H, $CH_2COO$, or $CH_2CH_2OH$; V', Y', Z', D', E' independently is nothing (or a pair electron), H (hydrogen), C1-C4 alkyl, a polyalkoxide group with 1 to 3 alkoxide units, O (oxygen), $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethyamine, or dimethylamidopropylamine (DMAPA) with the provisos that (1) the structure contains at least one amideoxide, betaine, or iminopropinate group, (2) V' and D' can not be nothing at the same time, and (3) the selection of Y', Z', and E' only allows the end nitrogen atom to be tertiary or quaternary.

The compositions of the invention can be prepared in the manner known to the skilled artisan, including but not limited to in-can and tank mix and application of the final formulation may be pre- or post-emergence. Post-emergence application results in particular advantages.

The VES drift control agent of the present invention can be added directly to a spray tank along with other ingredients. When used as a tank side additive, an effective amount of the drift control agent comprising at least one VES of the present invention is generally represented by weight concentrations of from 0.001% to 5.0%, in another embodiment from 0.01% to 1.0%. Likewise, when the VES of the present invention is used in a pesticide formulation (in-can), it is present at weight concentrations that will deliver from about 0.001% to 5.0% to the final use dilution, in another embodiment from about 0.01% to 1.0%, of the final use dilution.

Suitable herbicides include acetochlor, acifluorfen, aclonifen, alachlor, ametryn, amidosulfuron, aminopyralid, amitrole, anilofos, asulam, atrazine, azafenidin, azimsulfuron, benazolin, benfluralin, bensulfuron-methyl, bentazone, bifenox, binalafos, bispyribac-sodium, bromacil, bromoxynil, butachlor, butroxidim, cafenstrole, carbetamide, carfentrazone-ethyl, chloridazon, Chlorimuron-ethyl, chlorobromuron, chlorotoluron, chlorsulfuron, cinidon-ethyl, cinosulfuron, clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Fluorochloridone, Fluoroxypyr, Flurtamone, Fomesafen, Foramsulfuron, Glufosinate, Hexazinone, Imazamethabenz-m, Imazamox, mazapic, Imazapyr, Imazaquin, Imazethapyr, Imazosulfuron, Iodosulfuron, Ioxynil, Isoproturon, Isoxaben, Isoxaflutole, Lactofen, Lenacil, Linuron, Mefenacet, Mesosulfuron-Methyl, Mesotrione, Metamitron, Metazachlor, Methabenzthiazuron, Metobromuron, Metolachlor, Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyridate, Pyrithiobac, Quinclorac, Quinmerac, Rimsulfuron, Sethoxydim, Simazine, S-Metolachlor, Sulcotrione, Sulfentrazone, Sulfosulfuron, Tebuthiuron, Tepraloxydim, Terbuthylazine, Terbutryn, Thifensulfuron-methyl, Thiobencarb, Tralkoxydim, Tri-allate, Triasulfuron, Tribenuron-methyl, Triclopyr, Trifloxysulfuron, Trifluralin, Triflusulfuron-methyl, Tritosulfuron, and mixtures and combinations thereof. Preferred herbicides are Acetochlor, Atrazine, Dicamba, Glufosinate, Paraquat, and mixtures and combinations thereof. More preferred herbicides are glyphosate, Atrazine, Dicamba, and Glufosinate and mixtures and combinations thereof. The most preferred herbicides are salts of glyphosate and glufosinate-ammonium. When the herbicide is an acid, it can be used in the acid form, though it is preferred that the herbicide be in the salt form selected from at least one of the group of an amine, lithium, sodium, ammonium or potassium. It shall be pointed out that when a pesticide appears in the text as a general name without specifying the counterions, it means both its acid form and salt form through out the specification.

Another embodiment of the present invention is a fungicide formulation having improved drift control comprising VES in accordance with the invention. Examples of suitable fungicides are:

Acibenzolar-S-methyl, aldimorph, amisulbrom, anilazine, azaconazole, azoxystrobin, benalaxyl, benodanil, benomyl, benthiavalicarb, binapacryl, biphenyl, bitertanol, blasticidin-S, boscalid, bromuconazole, bupirimate, captafol, captan, carbendazim, carboxin, carpropamid, chloroneb, chlorothalonil, chlozolinate, copper, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, dinocap, dithianon, dodemorph, dodine, edifenphos, enestrobin, epoxiconazole, etaconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluoxastrobin, fluquinconazole, flusilazole, flusulfamide, flutolanil, flutriafol, folpet, fosetyl-Al, fthalide, fuberidazole, furalaxyl, furametpyr, guazatine, hexaconazole, hymexazole, imazalil, imibenconazole, iminoctadine, iodocarb, ipconazole, iprobenfos (IBP), iprodione, iprovalicarb, isoprothiolane, isotianil, kasugamycin, kresoxim-methyl, laminarin, mancozeb, mandipropamid, maneb, material of biological, mepanipyrim, mepronil, meptyldinocap, metalaxyl, metalaxyl-M, metconazole, methasulfocarb, metiram, metominostrobin, metrafenone, mineral oils, organic oils, myclobutanil, naftifine, nuarimol, octhilinone, ofurace, origin, orysastrobin, oxadixyl, oxolinic acid, oxpoconazole, oxycarboxin, oxytetracycline, pefurazoate, penconazole, pencycuron, penthiopyrad, phosphorous acid and, picoxystrobin, piperalin, polyoxin, potassium bicarbonate, probenazole, prochloraz, procymidone, propamocarb, propiconazole, propineb, proquinazid, prothiocarb, prothioconazole, pyraclostrobin, pyrazophos, pyribencarb, pyributicarb, pyrifenox, pyrimethanil, pyroquilon, quinoxyfen, quintozene (PCNB), salts, silthiofam, simeconazole, spiroxamine, streptomycin, sulphur, tebuconazole, teclofthalam, tecnazene (TCNB), terbinafine, tetraconazole, thiabendazole, thifluzamide, thiophanate, thiophanate-methyl, thiram, tiadinil, tolclofosmethyl, tolylfluanid, triadimefon, triadimenol, triazoxide, tricyclazole, tridemorph, trifloxystrobin, triflumizole, triforine, triticonazole, validamycin, valiphenal, vinclozolin, zineb, ziram, and zoxamide, and mixtures and combinations thereof.

Still another embodiment of the present invention is an insecticide formulation having improved drift control comprising VES in accordance with the invention. Examples of suitable insecticides are: kerosene or borax, botanicals or natural organic compounds (nicotine, pyrethrin, strychnine and rotenone), chorinated hydrocarbon (DDT, lindane, chlordane), organophosphates (malathion and diazinon), carbamates (carbaryl and propoxur), fumigants (naphthalene) and benzene (mothballs), synthetic pyrethroids, and mixtures and combinations thereof.

The above listings of specific pesticides are not intended to be inclusive of all possibilities.

Yet still another embodiment of the present invention is a mixture of any herbicide, fungicide, and insecticide selected form the above groups having improved drift control comprising VES in accordance with the invention.

The invention will now be illustrated by the following non-limiting examples.

Example 1

100 g of testing solution was prepared according to the composition of the following table. If the VES surfactant formed gel in water, heating (to ~60-70 C) was used to facilitate dissolution. Mixing was with a magnetic bar until the sample totally dissolved (or evenly dispersed). Order of adding was not critical. Data was recorded in notebook 2207-71.

In the following table, C1 means component 1, C2 component 2 and C3 component 3. Appr means appearance, Ki viscosity cP means kinematic viscosity in centipoise, measured by a U-shape viscometer, model Cannon 100 Z858.

VES-2C was a experimental blend comprising about 51% erucyl dimethyl amidopropyl betaine, DR-2000 was a commercial guar gum product used as drift control agent in agriculture, Ethoquad E/12 was erucyl 2-EO methyl chloride quaternary; Aromox APA-T was tallow dimethylamidopropyl amine (DMAPA), Arquad 16-29 was C16 trimethyl chloride quaternary (29% active in water), Arquad SV-60 was soya trimethyl chloride quaternary (60%), Arquad APA-E E was 80% erucyl dimethyl amidopropyl betaine, Arquad 2HT-83E was ~83% di-tallow dimethyl chloride quaternary, Arquad 2C-75 was 75% di-coco dimethyl chloride quaternary, and Roundup® Original was a commercial product from Monsanto containing isopropylamine salt of glyphosate and tallowamine ethoxylate.

| | Name of C1 | wt of C1 | wt of Water | Name of C2 | wt of C2 | Name of C3 | wt of C3 | Appr | Ki Visco cP | Surface tension mN/m |
|---|---|---|---|---|---|---|---|---|---|---|
| 1 | | | 99.9 | VES-2C | 0.1077 | | | C | 1.42 | 33.9 |
| 2 | | | 99.9 | DR-2000 Guar | 0.1008 | | | H | 3.41 | 45.03 |
| 3 | | | 99.9 | Erucid amido betaine | 0.1054 | | | I | | 34.13 |
| 4 | | | 99.9 | Ethoquad E/12 | 0.1154 | | | C | 0.98 | 37.2 |
| 5 | | | 99.9 | Aromox APA-T | 0.1065 | | | C | 1.02 | 32.54 |
| 6 | | | 99.9 | Arquad 16-29 | 0.1081 | Na salicylate | 0.02 | C | 2.07 | 33.07 |
| 7 | | | 99.9 | Arquad SV-60 | 0.1065 | Na salicylate | 0.02 | C | 2.27 | 32.81 |
| 8 | | | 99.9 | Arquad APA-E E | 0.0985 | | | C | 0.98 | 40.47 |
| 9 | | | 99.9 | Arquad 2HT-83E | 0.0999 | | | H | 1.38 | 33.57 |
| 10 | | | 99.9 | Arquad 2C-75 | 0.1011 | | | C | 0.99 | 28.54 |
| 11 | 62% IPA glyphosate | 1 | 98.9 | VES-2C | 0.0994 | | | C | 1.01 | 33.44 |
| 12 | 62% IPA glyphosate | 1 | 98.9 | DR-2000 Guar | 0.1009 | | | H | 3.52 | 47.47 |
| 13 | 62% IPA glyphosate | 1 | 98.9 | DR-2000 Guar | 0.1008 | Na salicylate | 0.02 | C | 3.31 | 43.83 |
| 14 | 62% IPA glyphosate | 1 | 98.9 | DR-2000 Guar | 0.1008 | Na salicylate | 0.02 | C | 3.45 | |
| 15 | 62% IPA glyphosate | 1 | 98.9 | Erucid amido betaine | 0.1008 | | | C | 3.31 | 31.71 |
| 16 | 62% IPA glyphosate | 1 | 98.9 | Ethoquad E/12 | 0.1052 | | | C | 0.98 | 36.98 |
| 17 | 62% IPA glyphosate | 1 | 98.9 | Ethoquad E/12 | 0.1129 | Na salicylate | 0.02 | C | 2.01 | 32.37 |
| 18 | 62% IPA glyphosate | 1 | 98.9 | Ethoquad E/12 | 0.1129 | Na salicylate | 0.02 | C | 3.21 | |

-continued

| | Name of C1 | wt of C1 | wt of Water | Name of C2 | wt of C2 | Name of C3 | wt of C3 | Appr | Ki Visco cP | Surface tension mN/m |
|---|---|---|---|---|---|---|---|---|---|---|
| 19 | 62% IPA glyphosate | 1 | 98.9 | Aromox APA-T | 0.0976 | | | C | 0.95 | 33 |
| 20 | 62% IPA glyphosate | 1 | 98.92 | Arquad 16-29 | 0.0774 | | | C | 0.95 | 40.9 |
| 21 | 62% IPA glyphosate | 1 | 98.92 | Arquad 16-29 | 0.0761 | Na salicylate | 0.02 | C | 1.06 | 31.59 |
| 22 | 62% IPA glyphosate | 1 | 98.92 | Arquad 16-29 | 0.0761 | Na salicylate | 0.02 | C | 0.98 | |
| 23 | 62% IPA glyphosate | 1 | 98.92 | Arquad SV-60 | 0.771 | | | C | 0.96 | 40.25 |
| 24 | 62% IPA glyphosate | 1 | 98.92 | Arquad SV-60 | 0.0871 | Na salicylate | 0.02 | C | 1.22 | 32.51 |
| 25 | 62% IPA glyphosate | 1 | 98.9 | VES-1 | 0.1095 | | | | | |
| 26 | 62% IPA glyphosate | 1 | 98.9 | Arquad APA-E E | 0.1048 | | | C | 1.01 | 38.9 |
| 27 | 62% IPA glyphosate | 1 | 98.9 | Arquad 2HT-83E | 0.0987 | | | I | | |
| 28 | 62% IPA glyphosate | 1 | 98.9 | Arquad 2C-75 | 0.0999 | | | H | 1.04 | 26.8 |
| 29 | 62% IPA glyphosate | 1 | 98.9 | Arquad 2C-75 | 0.1064 | Na salicylate | 0.02 | H | 1.12 | 26.54 |
| 30 | Roundup Original | 1.52 | 98.38 | VES-2C | 0.114 | | | C | 1.05 | 38.59 |
| 31 | Roundup Original | 1.52 | 98.38 | DR-2000 Guar | 0.1022 | | | H | 3.55 | 42.03 |
| 32 | Roundup Original | 1.52 | 98.38 | Erucid amido betaine | 0.0963 | | | C | 0.86 | 35.17 |
| 33 | Roundup Original | 1.52 | 98.38 | Ethoquad E/12 | 0.0994 | | | C | 0.86 | 39.61 |
| 34 | Roundup Original | 1.52 | 98.38 | Aromox APA-T | 0.0972 | | | C | 1.01 | 37.37 |
| 35 | Roundup Original | 1.52 | 98.4 | Arquad 16-29 | 0.0835 | | | C | 1.01 | 41.47 |
| 36 | Roundup Original | 1.52 | 98.4 | Arquad SV-60 | 0.0817 | | | C | 0.99 | 40.22 |
| 37 | Roundup Original | 1.52 | 98.38 | VES-1 | | | | | | |
| 38 | Roundup Original | 1.52 | 98.38 | Arquad APA-E E | 0.113 | | | C | 0.98 | 40.49 |
| 39 | Roundup Original | 1.52 | 98.38 | Arquad 2HT-83E | 0.1047 | | | I | | |
| 40 | Roundup Original | 1.52 | 98.38 | Arquad 2C-75 | 0.1045 | | | C | 1.01 | 31.68 |
| 41 | 50% ammonium glyphosate | 1 | 98.9 | VES-2C | 0.1101 | | | C | 0.96 | |
| 42 | 50% ammonium glyphosate | 1 | 98.9 | DR-2000 Guar | 0.0982 | | | I | | |
| 43 | 50% ammonium glyphosate | 1 | 98.9 | Erucid amido betaine | 0.0979 | | | I | | |
| 44 | 50% ammonium glyphosate | 1 | 98.9 | Ethoquad E/12 | 0.1057 | Na salicylate | 0.02 | C | 3.29 | |
| 45 | 50% ammonium glyphosate | 1 | 98.9 | Aromox APA-T | 0.0997 | | | C | 1.08 | |
| 46 | 50% ammonium glyphosate | 1 | 98.92 | Arquad 16-29 | 0.1119 | Na salicylate | 0.02 | C | 1.16 | |
| 47 | 50% ammonium glyphosate | 1 | 98.92 | Arquad SV-60 | 0.0853 | Na salicylate | 0.02 | C | 1.26 | |
| 48 | 50% ammonium glyphosate | 1 | 98.9 | Arquad APA-E E | 0.095 | | | C | 0.96 | |
| 49 | 50% ammonium glyphosate | 1 | 98.9 | Arquad 2HT-83E | 0.1074 | Na salicylate | 0.02 | I | | |

-continued

| Name of C1 | wt of C1 | wt of Water | Name of C2 | wt of C2 | Name of C3 | wt of C3 | Appr | Ki Visco cP | Surface tension mN/m |
|---|---|---|---|---|---|---|---|---|---|
| 50% ammonium glyphosate | 1 | 98.9 | Arquad 2C-75 | 0.0997 | Na salicylate | 0.02 | H | 0.95 | |

Surface tension measurements were also carried out at room temperature using the Kruss 12 tensiometer.

Example 2

Drift Repeatability Study

| | A 1% IPA glyphosate (62%) | B 1% IPA glyphosate (62%) + 0.1% DR-200 | C 1% IPA glyphosate (62%) + 0.1% Ethoquad E/12 + 0.02% Na salicylate | D 1% IPA glyphosate (62%) + 0.1% Erucyl DMAPA betaine | E Water only |
|---|---|---|---|---|---|
| 10 sec wt 1, g | 114.3 | 115.1 | 108.4 | 105.3 | |
| 10 sec wt 2, g | 117.6 | 113.4 | 107.2 | 118.8* | |
| 10 sec wt 3, g | 114.9 | 115.9 | 109.1 | 106.1 | |
| 10 sec wt 4, g | 110.2 | 112.5 | 110.6 | 105.8 | |
| Average wt, g | 114.25 | 114.225 | 108.825 | 105.7333333 | Not measured |
| Solution appearance | thin | thin | thick | thick | thin |
| Drift level | High level- poor | Small level | Medium level (some drift) - good | Medium level (some drift) - good | High level- poor |

Method: One gallon of each of the above samples (5 samples including water) was prepared. The water used was city tap water in all cases. Samples were prepared the day before testing to ensure that samples were solubilized.

Each sample was sprayed using the tub sprayer with the yellow nozzle (designated "XR teejet"). The spraying pressure used was 30 psi. The sample was prayed into a 5-gal plastic bucket for 10 seconds and the weight of the sprayed sample was recorded. Four replicates were made for each sample. The drift level was determined by observing the mist during 10 second spraying intervals.

The tub was cleaned by rinsing with tap water between samples.

The data in example 2 indicated that 1% IPA glyphosate (62%) (Sample A) and water (Sample E) had high level of drifting (a lot of mist). 1% WA glyphosate (62%)+0.1% DR-200 (Sample B) gave lowest level of drifting (least mist). Samples containing VES surfactants (Sample C and D) gave intermediate (desired) drift level between the guar only sample (Sample B) and 1% WA glyphosate (62%) sample (Sample A).

Example 3

Drift Observation with a Hand-Held Sprayer (Data Recorded in Notebook 2207-97)

| Name of C1 | wt of C1 | wt of H2O | Name of C2 | wt of C2 | Name of C3 | wt of C3 | Name of C4 | wt of C4 | Drift Pattern |
|---|---|---|---|---|---|---|---|---|---|
| 62% IPA glyphosate | 0.33 | 30 | | | | | | | fine |
| 62% IPA glyphosate | 0.33 | 30 | DR-2000 Guar | 0.033 | | | | | thin |
| 62% IPA glyphosate | 0.33 | 30 | DR-2000 Guar | 0.033 | Armeen APA 2 | 0.1 | | | thin |
| | | 30 | DR-2000 Guar | 0.033 | KCl | 0.06 | | | thin |
| 62% IPA glyphosate | 0.33 | 30 | DR-2000 Guar | 0.01 | | | | | fine |
| 62% IPA glyphosate | 0.33 | 30 | DR-2000 Guar | 0.01 | Ethoquad E/12 | 0.1 | | | T/F |

-continued

| Name of C1 | wt of C1 | wt of H2O | Name of C2 | wt of C2 | Name of C3 | wt of C3 | Name of C4 | wt of C4 | Drift Pattern |
|---|---|---|---|---|---|---|---|---|---|
| 62% IPA glyphosate | 0.33 | 30 | DR-2000 Guar | 0.01 | VES 2C | 0.1 | | | T/>F |
| 62% IPA glyphosate | 0.33 | 30 | corn starch | 0.1 | | | | | fine |
| 62% IPA glyphosate | 0.33 | 30 | DR-2000 Guar | 0.02 | | | | | >T/F |
| 62% IPA glyphosate | 0.33 | 30 | DR-2000 Guar | 0.01 | NS 500 LQ | 0.043 | | | T/>F |
| 62% IPA glyphosate | 0.33 | 30 | DR-2000 Guar | 0.01 | CO 360 | 0.051 | | | T/>F |
| 62% IPA glyphosate | 0.33 | 30 | DR-2000 Guar | 0.01 | Arquad APA E E | 0.077 | | | T/>F |
| 62% IPA glyphosate | 0.33 | 30 | DR-2000 Guar | 0.01 | TSP-15 | 0.051 | | | T/>F |
| 62% IPA glyphosate | 0.33 | 30 | DR-2000 Guar | 0.01 | corn starch | 0.01 | Ethoquad E/12 | 0.1 | T/>F |
| 62% IPA glyphosate | 0.33 | 30 | DR-2000 Guar | 0.01 | corn starch | 0.01 | VES 2C | 0.1 | T/>F |

Tests for drift were conducted using a hand-held sprayer (sprayer head cat. #30W8TS and sprayer bottle cat. #68WRT8). Test solutions were added to the bottle and the spray head was pumped several times with constant pressure until a consistent spray was produced.

The normal spray pattern with water appeared as a fine, broad pattern of mist (fine). Samples containing guar exhibited a different pattern, consisting of a thin, concentrated spray stream with almost no fine mist being observed (thin). Samples shown as T/F were a mix of the two patterns. ">F" means a very fine spray pattern was observed.

This method of spraying seemed sensitive and capable of picking up small changes in drift characteristics.

All samples containing guar contained small floating globules after initial mixing. Overnight, these globules settled to the bottom of the vial. We noticed that the spray pattern of the clear upper layer from the guar sample was the same as that of the original sprayed samples (thin).

We claim:

1. A pesticidal composition comprising (A) a pesticide and (B) an amount of a drift control agent effective to reduce drifting of drops of the composition to unintended targets while providing enhanced efficacy to the pesticide, wherein said drift control agent is the only enhancer of pesticide efficacy in the composition, wherein said drift control agent is a viscoelastic ethoxylated amineoxide with two ethylene oxide ("EO") units having the following structure:

wherein R is C18-C22 linear or branched, saturated or unsaturated hydrocarbon group.

2. The composition of claim 1 wherein said pesticide is selected from the group consisting of insecticides, fungicides, herbicides, and mixtures thereof.

3. The composition of claim 2 wherein said herbicide does not contain 2,4-dichlorophenoxyacetic acid ("2,4-D").

4. The composition of claim 1 wherein said pesticide is a herbicide selected from the group consisting of glyphosate, dicamba, atrazine, paraquat, and mixtures thereof.

5. The composition of claim 1 which additionally comprises at least one additional polymer selected from the group consisting of guar gum, xanthan gum, and polyacrylamide.

6. A method of reducing adverse drift in a pesticidal composition comprising a pesticide, said method comprising adding to said composition an amount of a drift control agent effective to reduce drifting of drops of the composition to unintended targets while providing enhanced efficacy to the pesticide, wherein said drift control agent is the only enhancer of pesticide efficacy in the composition, wherein said drift control agent is a viscoelastic ethoxylated amineoxide with 2 ethylene oxide ("EO") units having the following structure:

wherein R is C18-C22 linear or branched, saturated or unsaturated hydrocarbon group.

7. The method of claim 6 wherein said pesticide is selected from the group consisting of insecticides, fungicides, herbicides, and mixtures thereof.

8. The method of claim 7 wherein said herbicide does not contain 2,4-dichlorophenoxyacetic acid ("2,4-D").

9. The method of claim 6 wherein said pesticide is a herbicide selected from the group consisting of glyphosate, dicamba, atrazine, paraquat, and mixtures thereof.

10. A method of claim 6, wherein the drift control agent is added directly to a spray tank along with other ingredients of the pesticide composition.

11. A method of combatting pests with reduced drifting of a pesticidal composition employed for said combatting, said method comprising spraying on the pests or on an area from which it is desired to exclude such pests an effective amount of pesticidal composition according to claim 1.

* * * * *